United States Patent [19]

Cohen et al.

[11] Patent Number: 5,043,341
[45] Date of Patent: Aug. 27, 1991

[54] N-(2-HYDROXYCYCLOPENTYL)-1-ISOPROPYL-6-METHYLERGOLINE-8-CARBOXAMIDES

[75] Inventors: Marlene L. Cohen, Indianapolis; David W. Robertson, Greenwood, both of Ind.

[73] Assignee: Eli Lilly and Company, Indianapolis, Ind.

[21] Appl. No.: 508,324

[22] Filed: Apr. 11, 1990

[51] Int. Cl.$^5$ .................... A61K 31/48; C07D 457/06
[52] U.S. Cl. ...................................... 514/288; 546/69
[58] Field of Search ........................................ 514/288

[56] References Cited

U.S. PATENT DOCUMENTS 4,931,447 6/1990 Foreman et al. .................... 514/288

OTHER PUBLICATIONS

Berde et al., Ergot Alkoloids and Related Compounds 1978, pp. 35, 323–324.

Primary Examiner—Cecilia Shen
Attorney, Agent, or Firm—Robert A. Conrad; Leroy Whitaker

[57] ABSTRACT

This invention provides N-(2-hydroxycyclopentyl)-1-isopropyl-6-methylergoline-8-carboxamides useful for blocking 5HT$_2$ receptors in mammals having an excess of serotonin centrally or peripherally. The invention also provides methods for treating sexual dysfunction, hypertension, migraine, vasospasm, thrombosis, ischemia, depression, anxiety, sleep disorders and appetite disorders with a compound of the invention.

26 Claims, No Drawings

N-(2-HYDROXYCYCLOPENTYL)-1-ISOPROPYL-6-METHYLERGOLINE-8-CARBOXAMIDES

BACKGROUND OF THE INVENTION

Over the past decade, there has been considerable interest in developing agents which are serotonin (5HT) antagonists, including compounds which block 5HT$_2$ receptors. Such agents are useful in treating disease states in which an excess of serotonin is a major contributing cause. These disease states include hypertension, anorexia nervosa, depression, mania, carcinoid syndrome, migraine and vasospasm. Certain ergoline derivatives have been found to possess such activity; see, e.g., U.S. Pat. No. 3,580,916.

More recently, certain ergoline-8-carboxamides were found to be potent 5HT$_2$ receptor blockers. EPO Patent Application Publication 296,748 reports the biological activities for a number of such derivatives, including a cyclopentyl amide of Example 9 and a 2-hydroxycyclohexyl amide (of undefined stereochemistry) in Example 14.

The present invention is directed to the discovery that certain stereochemically pure 2-hydroxycyclopentyl amides of ergolines are potent 5HT receptor blockers superior to these art compounds in suppressing serotonin-induced increases in mean arterial pressure in vivo.

SUMMARY OF THE INVENTION

The present invention relates to two diastereomers of the general formula

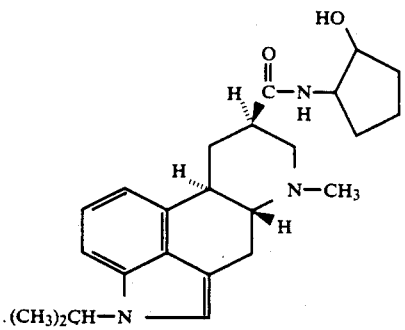

I and the pharmaceutically acceptable acid addition salts thereof.

The present invention also provides pharmaceutical formulations comprising, and methods of using, compounds of the invention.

DETAILED DESCRIPTION OF THE INVENTION

Compounds of the present invention are named as ergoline derivatives in which the trans-(−) or 5R,10R configuration of the bridgehead hydrogens is specified. This is the same configuration as in the naturally-occurring 9,10-dihydro ergot alkaloids. In U.S. Pat. No. 3,580,916, a different naming system is used. The basic ring system is named as a 6aR,10aR-4,6,6a,7,8,9,10,10a-octahydroindolo[4,3-f,g]quinoline. Illustratively, by the alternate naming system, 9,10-dihydrolysergic acid becomes 6aR,10aR-7-methyl-4,6,6a, 7,8,9,10,10a-octahydroindolo[4,3-f,g]quinoline-9β-carboxylic acid. Another equally valid name for dihydrolysergic acid is (8β)-6-methylergoline-8-carboxylic acid. The trivial name "ergoline" will be employed herein with the numbering system specified above for compounds of the invention.

The configuration at asymmetric carbons 5, 8, and 10 in the above formula is set as 5β, 8β and 10α, or 5R, 8R, 10R, referred to below as (R,R,R). The substituted cyclopentyl amide group contains two additional asymmetric carbon atoms. The 2-hydroxycyclopentylamine component of the target molecules can exist as two racemates, each racemate containing two enantiomers or stereoisomers. Thus, there is a pair of trans isomers and a pair of cis isomers:

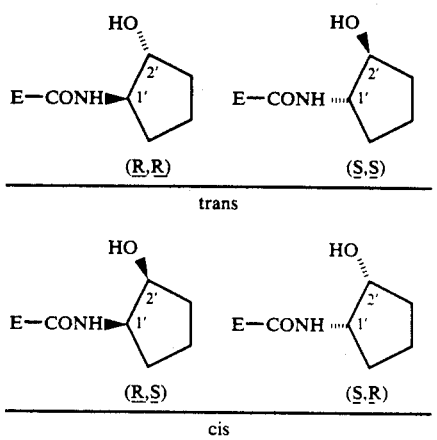

where E is the 1-isopropyl-6-methylergolin-8-yl portion of I. The trans isomers have an absolute configuration of (R,R) and (S,S) in the cyclopentyl ring; the cis isomers are designated (R,S) and (S,R). The compounds provided by this invention are only those having the (S) configuration at the cyclopentyl carbon atom attached to the ergoline amide. If the two chiral carbon atoms of the cyclopentyl ring are 1' and 2' as drawn above, the absolute configuration of the two compounds of this invention according to the 5,8,10,',2' convention is therefore, (R,R,R,S,S) and (R,R,R,S,R), the latter being preferred. Since the ergoline substructure is common to all of these compounds, such ergoline amides will simply be referred to as the (S,S) and (S,R) isomers, respectively. As will be discussed further, the (R,R) and (R,S) isomers have also been prepared.

Pharmaceutically acceptable acid addition salts of the compounds of the invention include salts derived from inorganic acids such as hydrochloric acid, nitric acid, phosphoric acid, sulfuric acid, hydrobromic acid, hydriodic acid, phosphorous acid and the like, as well as salts derived from organic acids such as aliphatic mono- and dicarboxylic acids, phenyl-substituted alkanoic acids, alkanedioic acids, aromatic acids, aliphatic and aromatic sulfonic acids, and the like. Such pharmaceutically acceptable salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, fluoride, acetate, propionate, caprylate, acrylate, formate, isobutyrate, caprate, heptanoate, propiolate, oxalate, malonate, succinate, suberate, sebacate, fumarate, maleate, mandelate, butyne-1,4-dioate, hexyne-1,6-dioate, benzoate, chlorobenzoate, methoxybenzoate, phthalate, terephthalate, benzenesulfonate, toluenesulfonate, chlorobenzenesulfonate, xylenesulfonate, phenylacetate, phenylpropionate, phenylbutyrate, citrate, lactate, β- hydroxybutyrate, glycollate, malate, tartrate, hippurate, lactobionate, methanesulfonate, propanesulfonate, naphthalene-1-sulfonate, naphthalene-2-sulfonate and like salts.

Preferred pharmaceutically acceptable acid addition salts are those formed with mineral acids such as hydrochloric acid.

The pharmaceutically acceptable acid addition salts of the compounds of this invention can also exist as various solvates, such as with water, methanol, ethanol, dimethylformamide, and the like. Mixtures of such solvates can also be prepared. The source of such solvate can be from the solvent of crystallization, inherent in the solvent of preparation or crystallization, or adventitious to such solvent. The hydrates are particularly useful, especially those of the hydrochloride salts.

The compounds of the present invention may be prepared by a variety of procedures well known to those of ordinary skill in the art. In particular, the procedures recited in EPO Patent Application Publication 296,748 are incorporated herein by reference as being useful for preparing the compounds of this invention.

Preferably, the appropriate dihydrolysergic acid is converted to the alkali metal salt and then to the ($C_1$-$C_4$ alkyl)formate derivative. This compound is finally reacted with the appropriate 2-hydroxycyclopentylamine to provide a compound of the invention. This reaction is represented by the following scheme:

ene, and the like. Commonly used bases include sodium or potassium hydride, sodium carbonate and especially potassium carbonate. This mixture is typically heated to form the alkali metal salt intermediate III. The mixture is next cooled and an equimolar to slight excess of a $C_1$-$C_4$ alkyl haloformate is added to the reaction mixture. After sufficient time to form the ($C_1$-$C_4$ alkyl)formate intermediate IV, typically approximately five to about 30 minutes, at least one equivalent of the desired 2-hydroxycyclopentylamine is added to the reaction mixture. Generally, the reaction is substantially complete after about two to about 200 hours when carried out at a temperature of about $-40°$ to about $50°$ C., preferably from about $-20°$ to about $25°$ C. The product of the reaction may be isolated by simply removing the reaction solvent, for instance by evaporation under reduced pressure. More typically, the reaction mixture containing the free base of the desired compound may be combined with water, and the product collected by filtration or extracted into a water immiscible solvent. The product thus isolated can be further purified if desired by any of several well known techniques. The compounds of the present invention may also be prepared by the reaction of 1-isopropyl-6-methylergoline-8-hydrazide with the desired 2-hydroxycyclopentylamine under conditions well known to those of ordinary skill in the art. This reaction may be represented by the following scheme:

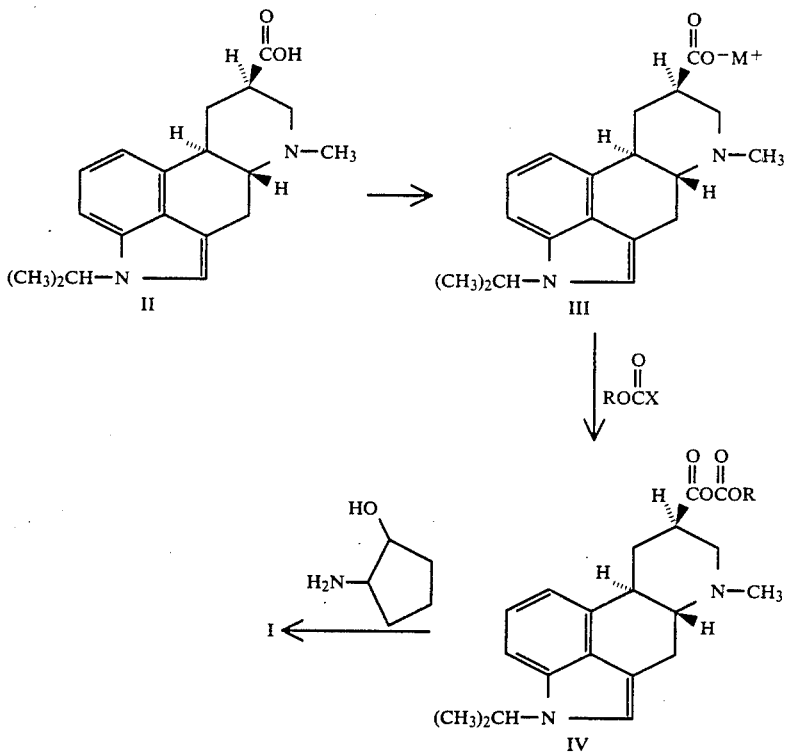

wherein R is $C_1$-$C_4$ alkyl, such as methyl, ethyl or preferably isobutyl, X is halogen, especially chloro, and M is an alkali metal.

The reaction can be carried out by combining the dihydrolysergic acid derivative II with about an equimolar quantity to slight excess of the base containing an alkali metal in a mutual solvent such tetrahydrofuran, diethyl ether, dichloromethane, dioxane, dimethylsulfoxide, N,N-dimethylformamide (DMF), benzene, tolu-

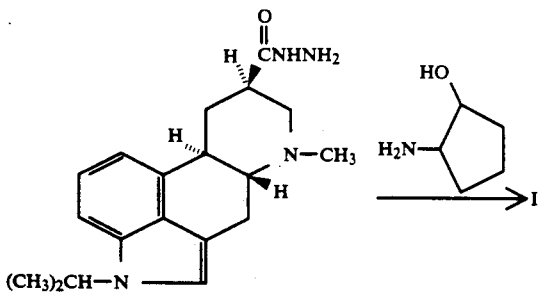

According to this procedure, the hydrazide starting material is dissolved in an aqueous acidic solution and the resulting mixture is cooled to a temperature in the range of about 0° C. to about 20° C. Typical acids suitable for use in this step of the process include the hydrohalic acids, such as hydrobromic acid and hydroiodic acid, and especially hydrochloric acid. To this mixture is added either sodium nitrite or sodium periodate, typically in an excess amount, and the mixture is made basic with a suitable base such as the inorganic bases, especially sodium bicarbonate. The intermediate formed by this reaction is isolated by extraction with a water immisible organic solvent, and an equimolar, to preferably an excess, of the desired 2-hydroxycyclopentylamine is combined with the solution containing the intermediate. The reaction is substantially complete within about one to 24 hours when conducted at a temperature in the range of about 0° C. to about 100° C., more preferably within about four to 12 hours when conducted at a temperature in the range of about 5° C. to about 20° C. The product is then isolated, typically by decanting or evaporating the volatile constituents under vacuum. The isolated product may then be further purified, if desired, by standard procedures.

The compounds of the present invention may also be prepared by the direct coupling of (8β)-1-isopropyl-6-methylergoline-8-carboxylic acid II with the appropriate 2-hydroxycyclopentylamine in the presence of a coupling reagent. This reaction may be represented by the following scheme:

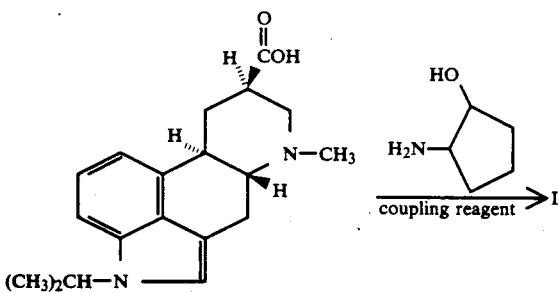

This reaction process necessitates the use of a coupling reagent, for example any of the type of coupling reagents commonly employed in the synthesis of peptides. Examples of such coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as 1-hydroxybenzotriazole mesylate or N-ethoxycarbonyl-2-ethoxy-1,2-dihydroquinoline (EEDQ). The direct coupling of the ergoline-8-carboxylic acid and amine is carried out by adding about an equimolar quantity of the amine starting material to a solution of the carboxylic acid in the presence of an equimolar quantity to slight excess of the coupling reagent. The reaction generally is carried out in an unreactive organic solvent such as dichloromethane, tetrahydrofuran (THF) or N,N-dimethylformamide (DMF), and is typically complete within about twenty-four hours when conducted at a temperature of about 0° to about 30° C. The product is then typically isolated by filtration. The product thus formed can be further purified, if needed, by any of several routine methods, including crystallization from common solvents, chromatography over solid supports such as silica or alumina, and related purification techniques.

The above schemes all depict preparation of the ergoline amides in a non-stereospecific manner. These processes may be performed using a mixture of the two racemates of 2-aminocyclopentanol, one or the other racemate, or the appropriate homochiral 2-aminocyclopentanol. In the former two cases, it will then be necessary to purify the resulting four or two isomers from each other to isolate one or both of the compounds of this invention. While this can be accomplished by fractional crystallization, it is preferred that such purifications be performed employing high pressure liquid chromatography. Although other conditions may also work, we have found that the use of a 0-10% methanol in methylene chloride gradient further containing 1% ammonium hydroxide over silica gel is effective to separate the ergoline amide isomers. Further purification, such as crystallization from methanol, can then be performed if desired.

To prepare the particular compounds of interest without separating the final products, one can also prepare the homochiral 2-aminocyclopentanols and employ them in any of the above reaction schemes. One particularly useful scheme is described in Example 2 below which can be employed in the preparation of both of the desired isomers. Briefly, cyclopentene oxide is allowed to react with (S)-(−)-alphamethylbenzylamine in a solvent such as water. The reaction produces both (R,R,S)- and (S,S,S)-2-[(1-phenylethyl)amino]cyclopentanol which can be separated by crystallization from hexanes. The pure (S,S,S)-intermediate is then catalytically hydrogenated, such as in the presence of palladium, in a non-reactive solvent, such as ethanol, to provide pure (S,S)-(+)-2-aminocyclopentanol. This versatile intermediate can be used in any of the above schemes to provide the (S,S) compound of this invention.

In addition, this intermediate can be acetylated with acetyl chloride in a solvent such as tetrahydrofuran in the presence of an acid scavenger, such as triethylamine, to give (S,S)-(+)-N-(2-hydroxycyclopentyl)acetamide. Treatment of this acetamide derivative with thionyl chloride results in the ring-closed intermediate (S,R)-4,5,6,6a-tetrahydro-2-methyl-3aH-cyclopentoxazole hydrochloride which is converted into (R,S)-(−)-2-aminocyclopentanol hydrochloride when allowed to reflux in the presence of dilute hydrochloric acid. This intermediate can then be used in any of the above schemes, preferably using the ergoline acid and carbonyldiimidazole, to give the (S,R) compound of this invention.

Alternatively, (S,S)-(+)-2-aminocyclopentanol can be prepared by treating cyclopentene oxide with ammonium hydroxide, preferably in the additional presence of a lower alkanol such as ethanol, to provide the trans racemate of 2-aminocyclopentanol. Fractional crystallization of the R-mandelic acid salt of the racemate resulted in the isolation of the R-mandelate salt of the (S,S) isomer of 2-aminocyclopentanol which can be converted into the free base by conventional means. This compound can then be used as described above for preparing the (S,S) compound of this invention, or subjected to further transformations to provide the (S,R) isomer.

The trans racemate of 2-aminocyclopentanol described above can also be converted into the cis racemate by treatment with acetyl chloride, cyclization to the cyclopentoxazole, and hydrolysis as described above. Either of these racemates can also be coupled to the ergoline carboxylic acid by methods as previously described to prepare the corresponding mixture of amides which can then be separated by, for example, high pressure liquid chromatography.

The pharmaceutically acceptable acid addition salts of the invention are typically formed by reacting an amine of the invention with an equimolar or excess amount of acid. The reactants are generally combined in a mutual solvent such as diethyl ether, benzene, or ethyl acetate, and the salt normally precipitates out of solution within about one hour to 10 days, and can be isolated by filtration.

The following Examples further illustrate the compounds of the present invention and methods of their synthesis. The Examples are not intended to be limiting to the scope of the invention in any respect and should not be so construed. Where structures were confirmed by mass spectral or proton nuclear magnetic resonance analysis, the compound is so designated by "MS" or "NMR", respectively.

EXAMPLE 1

(S,S)-N-(2-Hydroxycyclopentyl)-1-isopropyl-6-methylergoline-8-carboxamide

A. Preparation of trans-2-aminocyclopentanol

In each of three one-gallon containers with screw caps were placed 75 g of cyclopentene oxide, 250 ml of ethanol, and 1500 ml of ammonium hydroxide. The reactions were capped and allowed to stand at room temperature for four days. The solvents were removed in vacuo and the resulting oil was distilled at reduced pressure. A total of 170.19 g of the title intermediate was collected as a colorless oil with a boiling point of 93°-95° C. at 8 mm Hg pressure. NMR, MS.

Analysis for $C_5H_{11}NO$:
Calc.: C, 59.37; H, 10.96; N, 13.85;
Found: C, 58.69; H, 11.26; N, 14.18.

B Preparation of (S,S)-N-(2-hydroxycyclopentyl)-1-isopropyl-6-methylergoline-8-carboxamide To a suspension of 6.24 g of 1-isopropyl-6-methylergoline-8-carboxylic acid in 120 ml of dimethylformamide under a nitrogen atmosphere were added 3.2 g of 1,1'-carbonyldiimidazole. After stirring for approximately four hours, a solution of 2.02 g of trans-2-aminocyclopentanol in 40 ml of dimethylformamide was added with stirring. After stirring at room temperature overnight, the mixture was added to water. The resulting precipitate was extracted three times into methylene chloride. The combined organic extracts were washed with a saturated sodium chloride solution, dried over sodium sulfate, and concentrated in vacuo. The resulting solid was purified by preparative high pressure liquid chromatography over silica gel eluting with methylene chloride/methanol/ammonium hydroxide (100:10:1). The appropriate fractions containing the more mobile diastereomer were combined, concentrated to dryness, and crystallized from methanol to provide 1.15 g of the desired title isomer, m.p. 260°-263° C. NMR, MS.

Analysis for $C_{24}H_{33}N_3O_2$:
Calc.: C, 72.88; H, 8.41; N, 10.62;
Found C, 72.65; H, 8.41; N, 10.49.

The appropriate fractions containing the less mobile diastereomer were also combined, concentrated to dryness, and crystallized from ethyl acetate to provide 680 mg of the corresponding (R,R)-isomer, m.p. 250°-252° C.

EXAMPLE 2

(S,R)-N-(2-Hydroxycyclopentyl)-1-isopropyl-6-methylergoline-8-carboxamide

A. Preparation of trans-N-(2-hydroxycyclopentyl)acetamide

A solution of 30.3 g of trans-2-aminocyclopentanol in 900 ml of tetrahydrofuran under a nitrogen atmosphere was cooled by means of an external ice bath to approximately 10° C. Forty-five milliliters of triethylamine were added followed by the dropwise addition of a solution of 21.3 ml of acetyl chloride in 240 ml of tetrahydrofuran. The resulting mixture was stirred overnight at room temperature. The resulting precipitate was removed by filtration and the filtrate was concentrated in vacuo to provide 43.59 g of the title intermediate as a red oil.

B. Preparation of cis-4,5,6,6a-tetrahydro-2-methyl-3aH-cyclopentoxazole hydrochloride To 84 ml of thionyl chloride under a nitrogen atmosphere was added a solution of 42.9 g of the acetamide intermediate from Example 2A above in 145 ml of chloroform in dropwise fashion maintaining the temperature at 0° to −5° C. by means of an external ethanol/ice bath. After the addition was complete, the resulting dark solution was allowed to warm to room temperature and stirred for two hours. The solution was concentrated in vacuo and triturated four times with diethyl ether. The resulting dark oil was dissolved in 120 ml of chloroform, treated with decolorizing carbon, filtered, and concentrated in vacuo to provide 60.36 g of the desired title intermediate.

C. Preparation of cis-2-aminocyclopentanol hydrochloride

The 60.36 g of crude intermediate from Example 2B above were stirred with 566 ml of 10% hydrochloric acid solution at reflux for one hour. After cooling, the mixture was filtered and the filtrate was concentrated in vacuo. To the residue were added 200 ml of methanol and the mixture again concentrated in vacuo. Fifty milliliters of ethanol were added and the solution was placed in the refrigerator. The resulting precipitate was collected by filtration, washed with cold ethanol, and recrystallized from ethyl acetate/methanol to provide 20.18 g of the desired title intermediate, m.p. 182°-184° C.

D. Preparation of (S,R)-N-(2-hydroxycyclopentyl)-1-isopropyl-6-methylergoline-8-carboxamide Following the procedure of Example 1B above, 8.75 g of the ergoline carboxylic acid, 3.86 g of cis-2-aminocyclopentanol hydrochloride, and 4.54 g of carbonyldiimidazole were allowed to react in the additional presence of 3.9 ml of triethylamine. Following the usual workup and purification by high pressure liquid chromatography, 1.62 g of the (S,R) isomer were isolated as colorless crystals (from ethanol), m.p. 232°–234° C. NMR, MS.

Analysis for $C_{24}H_{33}N_3O_2$:
Calc.: C, 72.88; H, 8.41; N, 10.62;
Found: C, 72.61; H, 8.45; N, 10.37.

Later fractions were combined, concentrated, and crystallized from isopropanol to yield 700 mg of the corresponding (R,S) isomer, m.p. 236°–238° C.

EXAMPLE 3

Alternate preparation of (S,S)-N-(2-hydroxycyclopentyl)-1-isopropyl-6-methylergoline-8-carboxamide.

A. Preparation of [S,S,S-(−)]-2-[(1-phenylethyl)amino]cyclopentanol

A mixture of 350 ml of cyclopentene oxide, 516 ml of S-(−)-α-methylbenzylamine, and 64 ml of water was heated at reflux for 72 hours. After cooling to room temperature, 2500 ml of diethyl ether were added, the mixture dried over sodium sulfate, and the solution concentrated in vacuo. Two liters of hexanes were added and the mixture seeded with a crystal of the subtitled intermediate that had been previously obtained by preparative high pressure liquid chromatography as the more mobile diastereomer. After stirring overnight at room temperature, the resulting precipitate was collected by filtration. Two additional recrystallizations from hexanes afforded 155.76 g of the desired subtitle intermediate, m.p. 78°–80° C. NMR, MS. Optical rotation: $[\alpha]_{365}^{25} = -91.0°$ (c=0.01 g/ml, methanol)

Analysis for $C_{13}H_{19}NO$:
Calc.: C, 76.06; H, 9.33; N, 6.82;
Found: C, 76.14; H, 9.44; N, 6.79.

B. Preparation of [S,S-(+)]-2-aminocyclopentanol

A solution of 18.5 g of [S,S,S-(−)]-2-[(1-phenylethyl)amino]cyclopentanol in ethanol was hydrogenated in the presence of 5% palladium-on-carbon. The resulting reaction mixture was filtered and concentrated in vacuo to provide 8.5 g of the title intermediate as an oil which crystallized on standing. A portion of this material was converted to the hydrochloride salt in ethanol using 5 N hydrochloric acid. Crystallization from ethyl acetate/methanol gave the hydrochloride salt, m.p. 162°–164° C. NMR, MS.

Analysis for $C_5H_{11}NO \cdot HCl$:
Calc.: C, 43.64; H, 8.79; N, 10.18;
Found: C, 43.53; H, 8.82; N, 10.13.
Optical Rotation: $[\alpha]_{365}^{25} = +91.9°$ (c=0.01 g/ml, water)

Preparation of (S,S)-N-(2-hydroxycyclopentyl)-1-isopropyl-6-methylergoline-8-carboxamide Following the procedure of Example 1B, 1.56 g of the ergoline acid and 505 mg of the amino alcohol from Example 3B above were allowed to react providing 1.31 g of the desired title product.

EXAMPLE 4

Alternate preparation of (S,R)-N-(2-hydroxycyclopentyl)-1-isopropyl-6-methylergoline-8-carboxamide

A. Preparation of (S,S)-(+)-N-(2-hydroxycyclopentyl)acetamide

Following the procedure of Example 2A, 74.7 g of (S,S)-(+)-2-aminocyclopentanol were reacted with acetyl chloride to provide 107.9 g of the title intermediate as an oil which crystallized upon cooling. NMR.

B. Preparation of (R,S)-(−)-2-aminocyclopentanol hydrochloride

Following the procedures of Examples 2B and 2C above, 108.1 g of (S,S)-(+)-N-(2-hydroxycyclopentyl)acetamide were treated with 202 ml of thionyl chloride. The reaction was worked up to provide the crude cyclopentoxazole hydrochloride which was then added to 1060 ml of 2.5 N hydrochloric acid solution. Workup in the usual way and crystallization from ethyl acetate/methanol provided 52.93 g of the desired subtitle intermediate, m.p. 226°–228° C. NMR. A second crop from the filtrate provided an additional 7.53 g of material. Both crops were combined (60.44 g) and dissolved in 50 ml of warm water. The solution was basified with 36 ml sodium hydroxide solution and diluted with 1500 mL of diethyl ether. The organic solution was dried over three pounds of sodium sulfate, filtered, and concentrated in vacuo to provide 37.71 g of the desired title intermediate free base as a colorless oil.

C. Preparation of (S,R)-N-(2-hydroxycyclopentyl)-1-isopropyl-6-methylergoline-8-carboxamide Following the procedure of Example 1B, a suspension of 134.3 g of ergoline carboxylic acid in ml of dimethylformamide was treated with 69.7 g of 1,1'-carbonyldiimidazole and 43.26 g of (R,S)-(−)-2-aminocyclopentanol in 430 ml of dimethylformamide. Workup in the usual manner provided 114.78 g of the desired title product.

EXAMPLE 5

(S,R)-N-(2-Hydroxycyclopentyl)-1-isopropyl-6-methylergoline-8-carboxamide monohydrochloride monohydrate Thirty grams of the free base product of Example 4C above were stirred in 600 ml of ethanol. To the suspension were added 15.2 ml of a 5 N hydrochloric acid solution. Brief stirring and warming resulted in a homogeneous solution. The solution was concentrated in vacuo and the resulting solids crystallized from 250 ml ethanol and 25 ml of water to provide 24.98 g of the desired title product as colorless crystals, m.p. 248°–250° C. NMR, MS.

Analysis for $C_{24}H_{33}N_3O_2 \cdot HCl \cdot H_2O$:
Calc.: C, 64.06; H, 8.06; N, 9.34;
Found: C, 64.36; H, 7.84; N, 9.57.

EXAMPLES 6–10

The following salts were prepared in the same manner as described in Example 5 above employing the appropriate acid. Solvent(s) of recrystallization are in parentheses.

6. (S,R)-N-(2-hydroxycyclopentyl)-1-isopropyl-6-methylergoline-8-carboxamide (Z)-2-butenedioate (ethanol/diethyl ether), m.p. 158°–160° C. dec.

Analysis for $C_{28}H_{37}N_3O_6$:
Calc.: C, 65.73; H, 7.29; N, 8.21;
Found: C, 65.93; H, 7.35; N, 8.08.

7. (S,R)-N-(2-hydroxycyclopentyl)-1-isopropyl-6-methylergoline-8-carboxamide L-(+)-tartrate (ethanol), m.p. 210°–212° C. dec.

Analysis for $C_{28}H_{39}N_3O_8$;
Calc: C, 61.64; H, 7.20; N, 7.70;
Found: C, 61.43; H, 7.00; N, 7.65.

8. (S,R)-N-(2-hydroxycyclopentyl)-1-isopropyl-6-methylergoline-8-carboxamide D-(−)-mandelate (ethanol/water), m.p. 98°–105° C. dec.

9. (S,R)-N-(2-hydroxycyclopentyl)-1-isopropyl-6-methylergoline-8-carboxamide methanesulfonate (ethanol/diethyl ether), m.p. 200° C. dec.

10. (S,R)-N-(2-hydroxycyclopentyl)-1-isopropyl-6-methylergoline-8-carboxamide citrate (methanol), m.p. 222° C. dec.

As noted above, the compounds of the present invention are useful for blocking 5HT receptors, especially $5HT_2$ receptors, in mammals having an excess of serotonin centrally or peripherally. As such, this invention also provides a method of blocking 5HT receptors which comprises administering to a mammal having an excess of serotonin centrally or peripherally a 5HT blocking dose of a compound of the invention. This method is potentially useful in treating disease states in which an excess of circulating or locally released serotonin is a major contributing cause. These disease states include hypertension, thrombosis, vascular occlusive disease, migraine, vasospasm (both coronary and cerebral), ischemia, depression, anxiety, sleep disorders, appetite disorders, schizophrenia, complications of atherosclerosis, and bladder dysfunction.

The compounds of the invention show relatively slight affinity for other receptors such as $\alpha_1$, $\alpha_2$, $\beta$, histamine, carbachol and the like receptors, and thus are highly selective in their action.

In carrying out the methods of the invention, a compound of the invention is administered orally or parenterally to a mammal with an excess of locally released or circulating serotonin in which mammal it is desirable to block 5HT receptors in order to alleviate symptoms attributable to excessive serotonin levels such as, but not limited to, vascular occlusive disease, schizophrenia, depression, thrombosis, portal hypertension and migraine. For parenteral administration, a water soluble salt of the drug is dissolved in an isotonic salt solution and administered by the intravenous route. For oral administration, a pharmaceutically-acceptable salt of the drug is mixed with standard pharmaceutical excipients such as starch and loaded into capsules or made into tablets, each containing about 0.1 to about 100 mg of active drug. Dosage levels of from about 0.01–1000 mg/kg are effective in blocking 5HT receptors. Thus, the oral dosage would be administered 2–4 times per day, giving a daily dosage range of about 0.003 to about 10.0 mg/kg per day.

In order to demonstrate that the compounds of the invention block $5HT_2$ receptors, compounds were evaluated in pithed rats challenged with serotonin (5HT). In control animals, an increase in mean arterial pressure (MAP) is seen when approximately 0.02 mg/kg of 5HT is administered i.v. 60 minutes after the oral administration of distilled water as compared to the same animals before 5HT administration. This pressor response to 5HT can be blunted by administering a compound of this invention in water by gavage 60 minutes prior to 5HT administration. The animals are pithed 45 minutes after administration of vehicle or test compound and administered the 5HT fifteen minutes thereafter. This procedure is similar to that reported by Cohen et al., *J. Cardiovascular Pharmacology*, 11 (51), 525 (1988) except that groups of 3–7 normotensive rats were used for each experimental condition instead of spontaneously hypertensive rats. In addition to the evaluation of the compound of Example 2 of this invention, compounds of Examples 9 and 14 of EPO 296,748 were also evaluated using the same samples prepared as reported in that reference; Example 14, the 2-hydroxycyclohexylamide, was a mixture of various stereoisomers. All compounds were administered as the free base. The i.v. dose of serotonin required to increase mean arterial pressure 30 mmHg one hour following oral dosing of the compound or vehicle alone (control) was calculated; results are reported in Table 1.

TABLE 1

Inhibition of 5HT-Induced Pressor Response in Pithed Rats

| Compound Example No. | Dose of Compound (mg/kg, p.o.) | | | |
|---|---|---|---|---|
| | 0+ | 0.01 | 0.03 | 0.1 |
| 2 | 0.015(7)* 0.023(7) | 0.259(6) | 0.384(3) | >10.0(4) |
| 9** | 0.022(3) 0.028(3) | — | 0.041(3) | 5.8(3) |
| 14** | 0.013(4) | 0.022(4) | — | 0.223(3) |

*Dose of serotonin (mg/kg, i.v.) that produced an increase in mean arterial pressure of 30 mmHg in the number of rats indicated in parentheses. The $ED_{30}$ for serotonin was determined from linear regression analysis of the log dose vs. mmHg change in mean arterial pressure to serotonin using those points corresponding to the linear portion of the average dose response curves. Responses to serotonin were measured one hour after oral administration of test compound or vehicle.
+Five individual groups of vehicle treated rats were used in these comparisons. This permits an indication of the variability of control responses to serotonin.
**From EPO Patent Application Publication 296,748

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyland propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

Formulation 1

Hard gelatin capsules are prepared using the following ingredients:

| | Quantity (mg/capsule) |
|---|---|
| (S,R)-N-(2-hydroxycyclopentyl)-1-isopropyl-6-methylergoline-8-carboxamide hydrochloride monohydrate | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

| | Quantity (mg/tablet) |
|---|---|
| (S,S)-N-(2-hydroxycyclopentyl)-1-isopropyl-6-methylergoline-8-carboxamide maleate | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

An aerosol solution is prepared containing the following components:

| | Weight % |
|---|---|
| (S,R)-N-(2-hydroxycyclopentyl)-1-isopropyl-6-methylergoline-8-carboxamide tartrate | 0.25 |
| ethanol | 29.75 |
| Propellant 22 (chlorodifluoromethane) | 70.00 |
| Total | 100.00 |

The active compound is mixed with ethanol and the mixture added to a portion of the propellant 22, cooled to −30° C. and transferred to a filling device. The required amount is then fed to a stainless steel container and diluted with the remainder of the propellant. The valve units are than fitted to the container.

Formulation 4

Tablets each containing 60 mg of active ingredient are made as follows:

| | |
|---|---|
| (S,S)-N-(2-hydroxycyclopentyl)-1-isopropyl-6-methylergoline-8-carboxamide mandalate | 250 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

Formulation 5

Capsules each containing 80 mg of medicament are made as follows:

| | |
|---|---|
| (S,R)-N-(2-hydroxycyclopentyl)-1-isopropyl-6-methylergoline-8-carboxamide citrate | 80 mg |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

Formulation 6

Suppositories each containing 225 mg of active ingredient may be made as follows:

| | |
|---|---|
| (S,S)-N-(2-hydroxycyclopentyl)-1-isopropyl-6-methylergoline-8-carboxamide | 225 mg |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 7

Suspensions each containing 50 mg of medicament per 5 ml dose are made as follows:

| | |
|---|---|
| (S,R)-N-(2-hydroxycyclopentyl)-1-isopropyl-6-methylergoline-8-carboxamide napsylate | 50 mg |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

Formulation 8

An intravenous formulation may be prepared as follows:

| | |
|---|---|
| (S,R)-N-(2-hydroxycyclopentyl)-1-isopropyl-6-methylergoline-8-carboxamide hydrochloride | 100 mg |
| isotonic saline | 1000 ml |

We claim:

1. A method of blocking 5HT receptors which comprises administering to a mammal having an excess of serotonin centrally or peripherally a 5HT blocking dose of (S,S)-N-(2-hydroxycyclopentyl)-1-isopropyl-6-methylergoline-8-carboxamide or a solvate or a pharmaceutically acceptable acid addition salt thereof.

2. A method of blocking 5HT receptors which comprises administering to a mammal having an excess of serotonin centrally or peripherally a 5HT blocking dose of (S,R)-N-(2-hydroxycyclopentyl)-1-isopropyl-6-methylerogoline-8-carboxamide or a solvate or a pharmaceutically acceptable acid addition salt thereof.

3. A method of treating hypertension in mammals which comprises administering to a hypertensive mammal a hypotensive dose of (S,S)-N-(2-hydroxycyclopentyl)-1-isopropyl-6-methylergoline-8-carboxamide or a solvate or a pharmaceutically acceptable acid addition salt thereof.

4. A method of treating hypertension in mammals which comprises administering to a hypertensive mammal a hypotensive dose of (S,R)-N-(2-hydroxycyclopentyl)-1-isopropyl-6-methylergoline-8-carboxamide or a solvate or a pharmaceutically acceptable acid addition salt thereof.

5. A method of treating migraine in mammals which comprises administering to a mammal suffering from migraine a migraine relieving dose of (S,S)-N-(2-hydroxycyclopentyl)-1-isopropyl-6-methylergoline-8-carboxamide or a solvate or a pharmaceutically acceptable acid addition salt thereof.

6. A method of treating migraine in mammals which comprises administering to a mammal suffering from migraine a migraine relieving dose of (S,R)-N-(2-hydroxycyclopentyl)-1-isopropyl-6-methylergoline-8-carboxamide or a solvate or a pharmaceutically acceptable acid addition salt thereof.

7. A method of treating vasospasm in mammals which comprises administering to a mammal experiencing vasospasm a vasospasm relieving dose of (S,S)-N-(2-hydroxycyclopentyl)-1-isopropyl-6-methylergoline-8-carboxamide or a solvate or a pharmaceutically acceptable acid addition salt thereof.

8. A method of treating vasospasm in mammals which comprises administering to a mammal experiencing vasospasm a vasospasm relieving a dose of (S,R)-N-(2-hydroxycyclopentyl)-1-isopropyl-6-methylergoline-8-carboxamide or a solvate or a pharmaceutically acceptable acid addition salt thereof.

9. A method of treating thrombosis in mammals which comprises administering to a mammal subject to thrombotic episodes a thrombosis alleviating dose of (S,S)-N-(2-hydroxycyclopentyl)-1-isopropyl-6-methylergoline-8-carboxamide or a solvate or a pharmaceutically acceptable acid addition salt thereof.

10. A method of treating thrombosis in mammals which comprises administering to a mammal subject to thrombotic episodes a thrombosis alleviating dose of (S,R)-N-(2-hydroxycyclopentyl)-1-isopropyl-6-methylergoline-8-carboxamide or a solvate or a pharmaceutically acceptable acid addition slat thereof.

11. A method of treating ischemia in mammals which comprises administering to a mammal suffering from ischemia an ischemia relieving dose of (S,S)-N-(2-hydroxycyclopentyl)-1-isopropyl-6-methylergoline-8-carboxamide or a solvate or a pharmaceutically acceptable acid addition salt thereof.

12. A method of treating ischemia in mammals which comprises administering to a mammal suffering from ischemia an ischemia relieving dose of (S,R)-N-(2-hydroxycyclopentyl)-1-isopropyl-6-methylergoline-8-carboxamide or a solvate or a pharmaceutically acceptable acid addition salt thereof.

13. A method of treating depression in mammals which comprises administering to a depressed mammal an antidepressant dose of (S,S)-N-(2-hydroxycyclopentyl)-1-isopropyl-6-methylergoline-8-carboxamide or a solvate or a pharmaceutically acceptable acid addition salt thereof.

14. A method of treating depression in mammals which comprises administering to a depressed mammal an antidepressant dose of (S,R)-N-(2-hydroxycyclopentyl)-1-isopropyl-6-methylergoline-8-carboxamide or a solvate or a pharmaceutically acceptable acid addition salt thereof.

15. A method of treating anxiety in mammals comprising administering to a mammal suffering from anxiety an antianxiety dose of (S,S)-N-(2-hydroxycyclopentyl)-1-isopropyl-6-methylergoline-8-carboxamide or a solvate or a pharmaceutically acceptable acid addition salt thereof.

16. A method of treating anxiety in mammals which comprises administering to a mammal, suffering from anxiety an antianxiety dose of (S,R)-N-(2-hydroxycyclopentyl)-1-isopropyl-6-methylergoline-8-carboxamide or a solvate or a pharmaceutically acceptable acid addition salt thereof.

17. A method of treating sleep disorders in mammals comprising administering to a mammal experiencing sleep disorders a sleep disorder relieving dose of (S,S)-N-(2-hydroxycyclopentyl)-1-isopropyl-6-methylergoline-8-carboxamide or a solvate or a pharmaceutically acceptable acid addition salt thereof.

18. A method of treating sleep disorders in mammals comprising administering to a mammal experiencing sleep disorders a sleep disorder relieving dose of (S,R)-N-(2-hydroxycyclopentyl)-1-isopropyl-6-methylergoline-8-carboxamide or a solvate or a pharmaceutically acceptable acid addition salt thereof.

19. A method of suppressing appetite in mammals comprising administering to a mammal in need of appetite suppression an appetite suppressing dose of (S,S)-N-(2-hydroxycyclopentyl)-1-isopropyl-6-methylergoline-8-carboxamide or a solvate or a pharmaceutically acceptable acid addition salt thereof.

20. A method of suppressing appetite in mammals comprising administering to a mammal in need of appetite suppression an appetite suppressing dose of (S,R)-N-(2-hydroxycyclopentyl)-1-isopropyl-6-methylergoline-8-carboxamide or a solvate or a pharmaceutically acceptable acid addition salt thereof.

21. A method of treating schizophrenia in mammals comprising administering to a mammal suffering from schizophrenia a schizophrenia relieving dose of (S,S)-N-(2-hydroxycyclopentyl)-1-isopropyl-6-methylergoline-8-carboxamide or a solvate or a pharmaceutically acceptable acid addition salt thereof.

22. A method of treating schizophrenia in mammals comprising administering to a mammal suffering from schizophrenia a schizophrenia relieving dose of (S,R)-N-(2-hydroxycyclopentyl)-1-isopropyl-6-methylergoline-8-carboxamide or a solvate or a pharmaceutically acceptable acid addition salt thereof.

23. A method of treating vascular occlusive disease in mammals comprising administering to a mammal suffering from vascular occlusive disease a vascular occlusive disease relieving dose of (S,S)-N-(2-hydroxycyclopentyl)-1-isopropyl-6-methylergoline-8-carboxamide or a solvate or a pharmaceutically acceptable acid addition salt thereof.

24. A method of treating vascular occlusive disease in mammals comprising administering to a mammal suffering from vascular occlusive disease a vascular occlusive disease relieving dose of (S,R)-N-(2-hydroxycyclopentyl)-1-isopropyl-6-methylergoline-8-carboxamide or a solvate or a pharmaceutically acceptable acid addition salt thereof.

25. A method of treating complications of atherosclerosis in mammals comprising administering to a mammal suffering from complications of atherosclerosis an effective dose of (S,S)-N-(2-hydroxycyclopentyl)-1-isopropyl-6-methylergoline-8-carboxamide or a solvate or a pharmaceutically acceptable acid addition salt thereof.

26. A method of treating complications of atherosclerosis in mammals comprising administering to a mammal suffering from complications of atherosclerosis an effective dose (S,R)-N-(2-hydroxycyclopentyl)-1-isopropyl-6-methylergoline-8-carboxamide or a solvate or a pharmaceutically acceptable acid addition salt thereof.

* * * * *